United States Patent [19]

Abrams et al.

[11] Patent Number: 5,679,778
[45] Date of Patent: Oct. 21, 1997

[54] MOLECULE LABELLING USING 2-HYDRANINOPYRIDINE DERIVATIVES

[75] Inventors: Michael J. Abrams, Glenmore; Gary J. Bridger, West Chester, both of Pa.; David A. Schwartz, Encinitas, Calif.; Sreenivasan Padmanabhan, Exton, Pa.; Michael E. Ultee, Belle Mead, N.J.

[73] Assignee: Johnson Matthey Public Limited Company, London, England

[21] Appl. No.: 432,204

[22] PCT Filed: Nov. 3, 1993

[86] PCT No.: PCT/GB93/02259

§ 371 Date: Jun. 30, 1995

§ 102(e) Date: Jun. 30, 1995

[87] PCT Pub. No.: WO94/10149

PCT Pub. Date: May 11, 1994

[30] Foreign Application Priority Data

Nov. 5, 1992 [GB] United Kingdom ............ 23168

[51] Int. Cl.$^6$ .................. C07D 213/82; A61K 31/44
[52] U.S. Cl. .................. 530/391.5; 534/14; 546/264; 546/306
[58] Field of Search ................ 546/366, 264; 514/353; 530/391.5; 534/14

[56] References Cited

U.S. PATENT DOCUMENTS 4,861,869  8/1989  Nicolotti et al. .......... 530/402
5,112,953  5/1992  Gustavson et al. .......... 530/391.5

FOREIGN PATENT DOCUMENTS 247866   12/1987  European Pat. Off. .
384769    8/1990  European Pat. Off. .
91 09876  7/1991  WIPO .

Primary Examiner—Zinna Northington Davis
Attorney, Agent, or Firm—Cushman Darby & Cushman IP Group Pillsbury Madison & Sutro LLP

[57] ABSTRACT

A compound of formula I

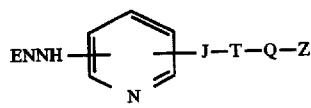

in which E is an alkenyl group or represents $H_2$ in which case the compound is in acid addition salt form, J is selected from —CO—NH—, —CO—O—, —CO—S— and —NH—CO—, T is an alkylene chain, or, if J is —CO—NH—, T is the residue of an amino acid moiety, Q is a hydrophilic or cleavable moiety, and Z is an amine- and/or thiol-reactive moiety. Conjugates formed by reacting such compound with a macromolecule, e.g. an immunoglobulin, and labelled macromolecules comprising a metal atom bound to such conjugate are also disclosed.

27 Claims, 7 Drawing Sheets

5 R=R¹=H
6 R=H, R¹=NO₂
7 R=CH₃, R¹=H

8 X = NH
9 X = O

MOLECULE LABELLING USING 2-HYDRANINOPYRIDINE DERIVATIVES

This is a 371 application of PCT/GB93/02259, filed Nov. 3, 1993.

The present invention concerns improvements in molecule labelling and more especially concerns novel bifunctional hydrazine derivatives which are capable of linking metal ions, particularly technetium and rhenium, to biologically useful molecules.

BACKGROUND OF THE INVENTION

Because of their high biological specificity, certain macromolecules (eg. monoclonal antibodies and fragments thereof) have been used to target radioisotopes to specific in vivo sites for the purpose of imaging and/or therapy. The use of the metastable isotope of technetium, $^{99m}$Tc, in diagnostic nuclear medicine is well established and the beta-emitting isotopes of rhenium $^{186}$Re, $^{188}$Re and $^{189}$Re can be used therapeutically. A number of methods for attaching technetium to macromolecules have been described. Some of these methods involve the reduction of disulphide groups in the macromolecule (usually an immunoglubulin) to thiols and the subsequent use of these groups to bind reduced Tc (eg. McKenzie et al, International Patent Publication WO 87/04164 and Bremmer et al, EP 0 271 806 A2). Direct labelling methods of this type have several potential disadvantages. The reduction of disulphide units can lead to protein de-naturation and a subsequent loss in biological specificity. Also, the method cannot be used to label macromolecules lacking disulphide moieties.

Alternatively, $^{99m}$Tc can be linked to macromolecules via bifunctional chelates such as DTPA (D. Lanteigne and D. J. Hnatowich, Int. J. Appl. Radiat. Isot., 35, 617, (1984)), chelating thiosemicarbazones (Y. Arano et al, Int. J. Nucl. Med. Biol., 12, 425, (1985)) and diamidedithiol ligands (A. Fritzberg, European Patent Appl, EP 188 256 2A). Problems associated with these methods include significant nonspecific binding of technetium (binding to the protein at sites other than the chelating group) and slow kinetics of Tc-labelling.

We have previously described, in European Patent Application EP 0 384 769 A2, a novel method of modifying biological molecules (eg. monoclonal antibodies, polyclonal human IgG and ovalbumin) and smaller molecules (eg. peptides) with 2-hydrazinopyridino moieties which react with reduced Tc, eg $^{99m}$Tc$^v$(glucoheptonate) to produce stable immunoreactive radioconjugates.

It has been demonstrated that biological molecules, (eg. monoclonal antibodies), modified to carry radioisotopes or drug molecules are metabolised in vivo and the resulting products are distributed throughout the body. In an effort to control the biodistribution of the metabolised products the chemical characteristics of the modification moiety have been altered by including hydrophilic or cleavable functionalities. Paik et al (J. Nucl. Med., 30, 1693–1701 (1989) and Antibod. Immunoconjug. and Radiopharm. 3, 127–136 (1990) have demonstrated that interposition of an ester functionality between the monoclonal antibody and the radioisotope ($^{111}$In) accelerated the isotope's blood clearance and reduced its uptake in normal organs such as muscle, kidney, liver and spleen. This faster clearance from normal organs increased the tumour/normal organ ratios 2–3 fold. Similarly enahnced clearance in non-tumoured animals was seen by Deshapande et al (Nucl. Med. Biol, 16, 587–597 (1989), Paik et al (Nucl. Med. Biol., 16, 475–481 (1989)). Weber et al (Bioconjugate Chem., 1, 431–437 (1990)), and Gustavson et al (U.S. Pat. No. 5,112,953 (1992) for antibodies labelled with $^{111}$In or $^{99m}$Tc radioisotopes via a chelator attached through an ester or disulphide function.

It is the object of the present invention to provide new bifunctional molecules having hydrazino groups and reactive groups spaced by hydrophilic and/or cleavable moieties which can be used to link metal ions, such as $^{99m}$Tc, to macromolecules so as to alter advantageously the biodistribution of the radiolabelled biological molecules.

SUMMARY OF THE INVENTION

According to the invention, novel bifunctional hydrazine compounds containing hydrophilic (eg acid) and/or cleavable moieties (eg disulphides and esters), as well as conjugates thereof, are provided. In vivo results demonstrating tumour localisation of $^{99m}$Tc Labelled conjugates of compounds according to the invention with the F(ab)' fragment of monoclonal antibody C46.3 are presented below. Some of the compounds show markedly improved tumour/blood values compared to the same antibody fragment labelled via the direction method (eg Bremmer et al).

The present invention provides novel compounds of the general formula I,

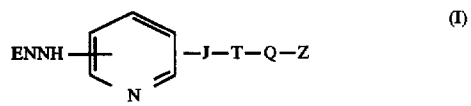

in which

E is an alkylidene group or represents H$_2$ in which case the compound is in an acid addition salt form, J is selected from the group consisting of —CO—NH—, —CO—O—, —CO—S— and —NH—CO—, T is an alkylene chain, or, if J is —CO—NH—, T is the residue of an amino acid moiety, Q is hydrophilic or cleavable moiety, and Z is an amine- and/or thiol-reactive moiety, or Q and Z together form a group which has both hydrophilic or cleavable and amine- and/or thiol-reactive functions.

Where E is alkylidene, it may be straight or branched lower alkylidene of up to four carbon atoms.

Suitably, Z is thiol-reactive, such as a bromoacetate, maleimido or disulphide or is amine-reactive, such as N-hydroxysuccinimidyl ester. The moiety Q may be a disulphide, ester or thioester.

As specified above, when the compound of formula I is in acid addition salt form, the acid is suitably a hydrohalic acid, nitric acid, trifluoroacetic acid, tetrafluoroboric acid or sulphuric acid, but other acids may be used providing these do not interfere with the use of the compounds.

The compounds of the invention may be synthesised by the skilled organic chemist. The molecules may be assembled in many different ways from various starting materials generally known per se. Conveniently, one of the reaction schemes set out in the accompanying drawings, schemes 1 to 4 or an obvious modification thereof is used. It will be readily appreciated that with molecules of this type, the precise starting materials and reaction conditions may be varied to give analogous processes yielding analogous products which fall within formula I. More particularly, details of the synthesis of specific compounds of formula I are given in the Examples hereinafter.

The invention also provides novel compounds of general formula II,

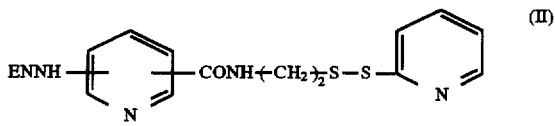

(II)

in which E is defined above. These compounds may also find utility as linker molecules.

The invention further provides a conjugate formed by the reaction of a macromolecule with a compound according to the invention. Suitably, the macromolecule is a protein such as an immunoglobulin, for example a monoclonal antibody, or a fragment thereof. This may be achieved by a method analogous to that described by Abrams et al in J. Nucl. Med., 31, 2022 (1990). Abrams et al also describe a method of radiolabelling, and in analogous manner, the conjugates of the invention may be used to produce an inventive and useful labelled macromolecule which is a metal atom, such as $^{99m}$Tc or a radioisotope of Re, bound to a conjugate according to the invention.

As will be described in more detail hereinafter, tests on $^{99m}$Tc-labelled antibody fragment conjugates show improvements over labelled fragments which do not utilise a linker molecule according to the invention or over labelled fragments utilising different linker molecules, in one or more of the characteristics of the ratio of radioactivity detected in the tumour to that in the blood, tumour to organs or clearance from the blood. Accordingly, the invention additionally provides the use of labelled macromolecules according to the invention for imaging and/or therapy, according to generally known principles.

The invention will now be further described in the following Examples, which are intended to be illustrative and not limiting.

EXPERIMENTAL

The $^1$H NMR spectra were recorded on an 300 MHz Bruker AM 300 Spectrometer. All $^1$H NMR spectra were recorded in DMSO-$d_6$ unless otherwise indicated.

Fast Atom Bombardment Mass Spectral analysis was carried out on a VG Analytical ZAB 2-SE high field mass spectrometer operating at Bacc=8 kV.

Compound names given in brackets [] in the various examples conform to Chemical Abstracts Serve Registry Index nomenclature.

6-Hydrazinonicotinic acid, 6-(BOC-hydrazine)nicotinic acid and succinimidyl 6-(BOC-hydrazine)nicotinate were prepared according to Abrams et al, J. Nucl. Med., 31, 2022 (1990).

BRIEF DESCRIPTION OF THE DRAWINGS

The structures of the individual compounds prepared in the following Examples are given in the attached drawings, in which the compound numbers correspond to the Example numbers.

EXAMPLE 1

6-(BOC-Hydrazine)nicotinamido-γ-t-butyl-(L)-glutamic Acid

Figure 1:
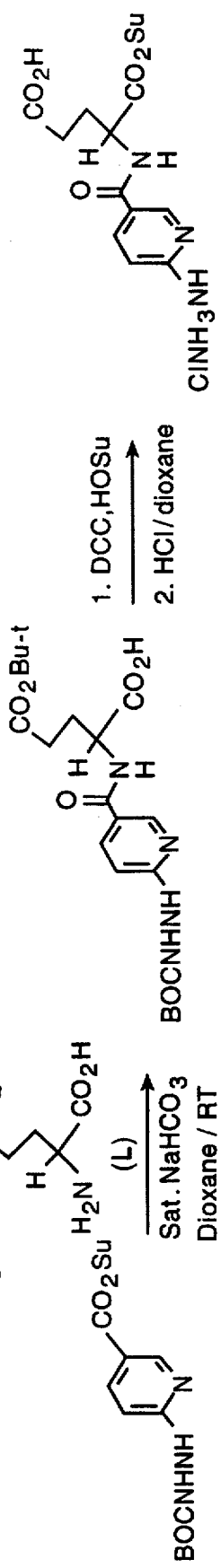
Figure 1:
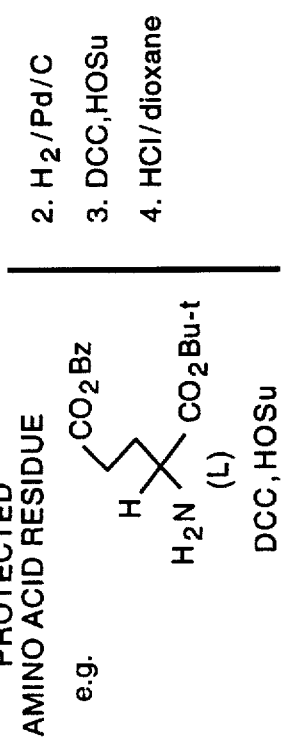
Figure 1:
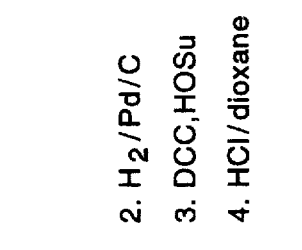
Figure 1:
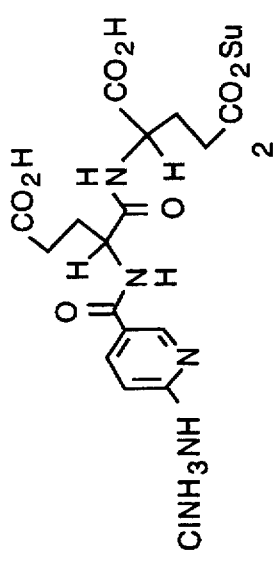
Figure 1:
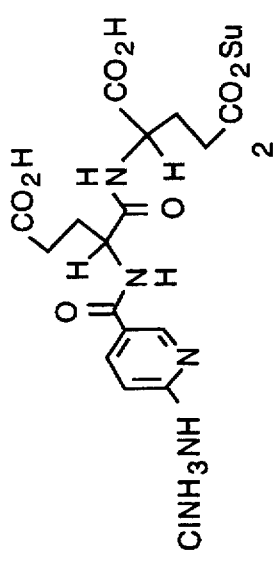
Figure 2:
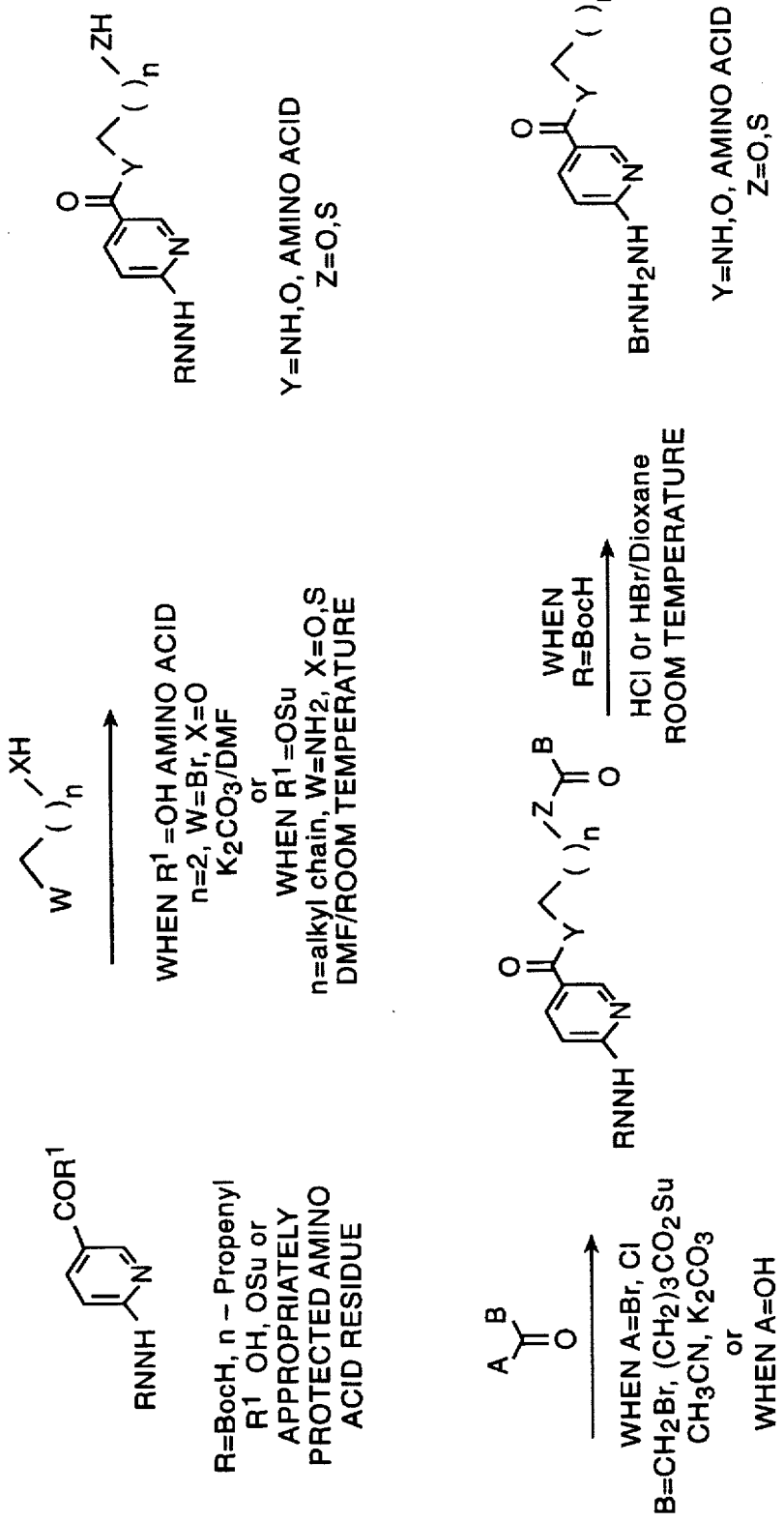
Figure 3:
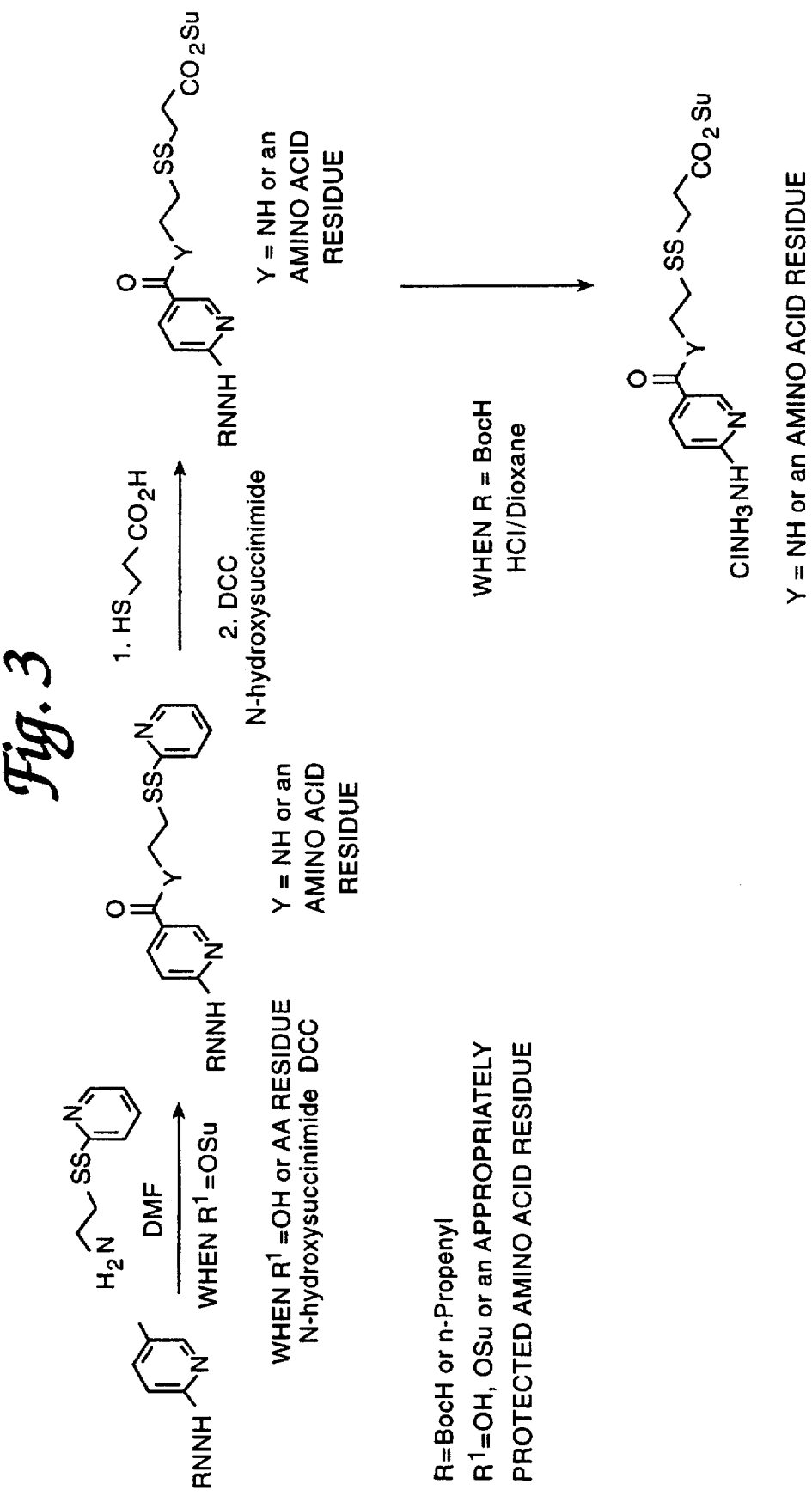
Figure 4A:
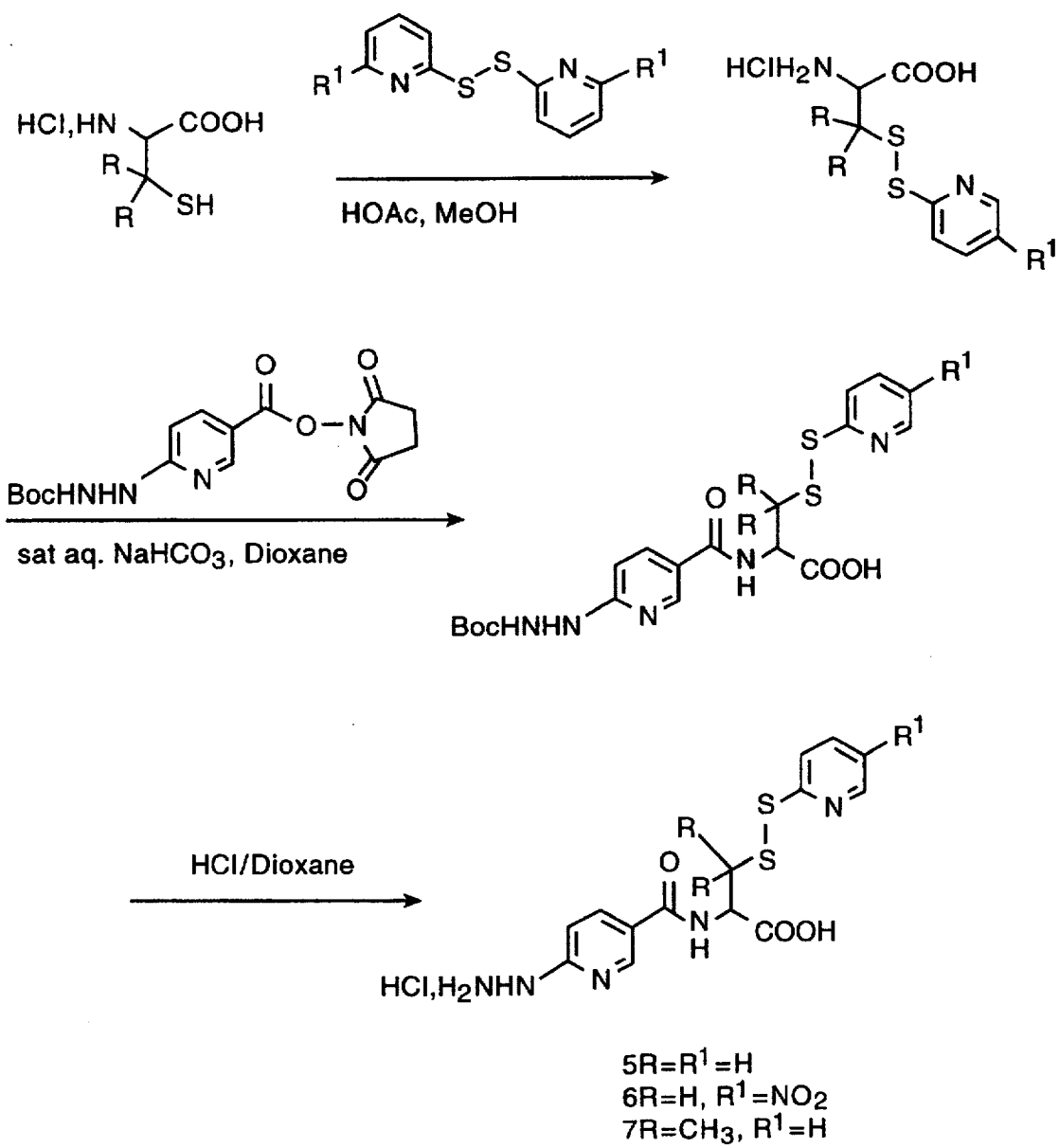
Figure 4B:
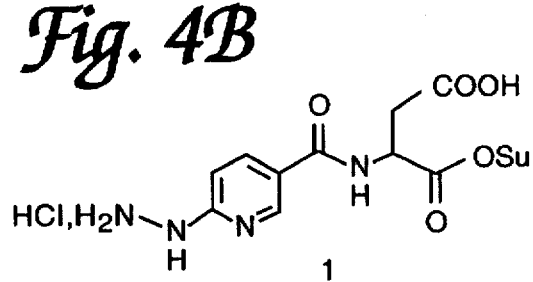
Figure 4C:
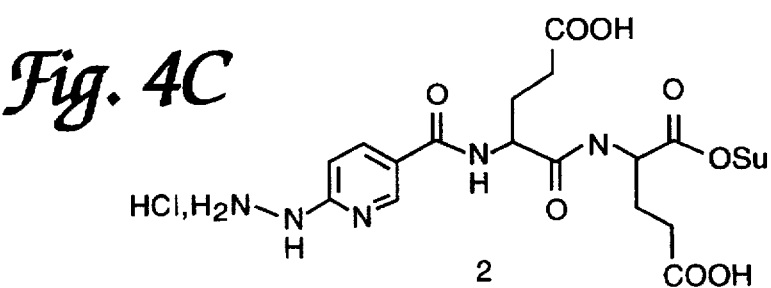
Figure 4D:
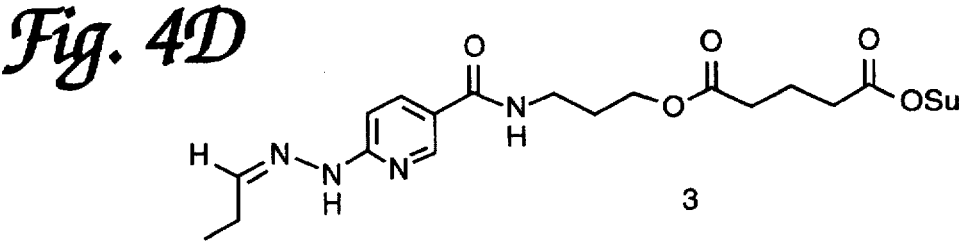
Figure 4E:
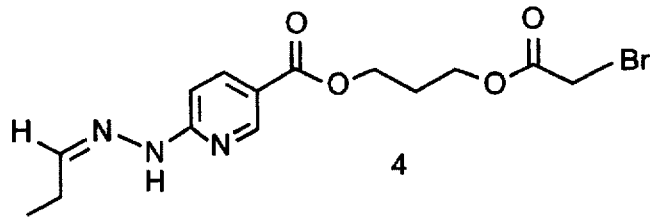
Figure 4F:
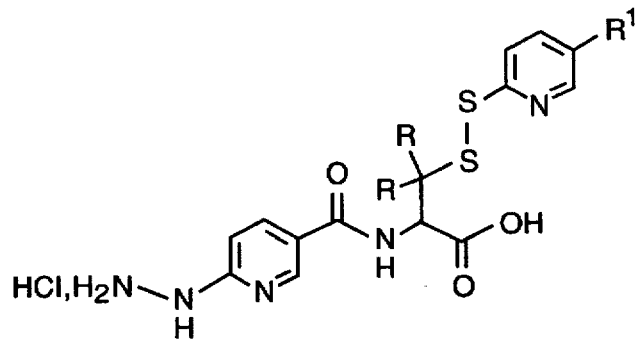
Figure 4G:
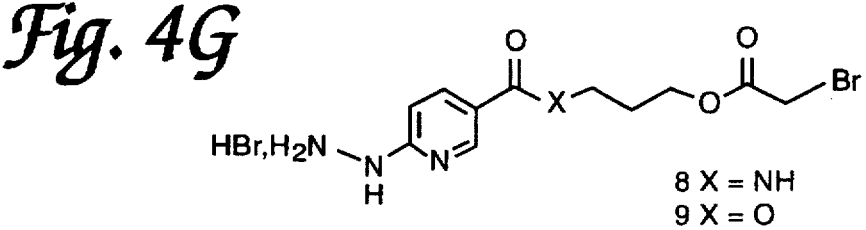
Figure 4H:
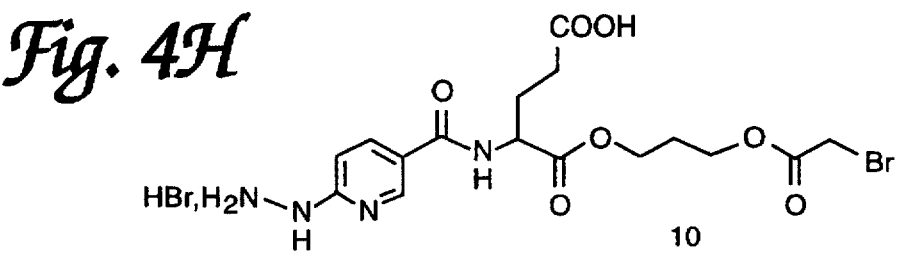
Figure 4I:
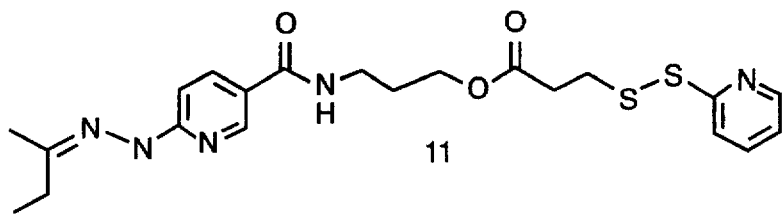
Figure 4J:
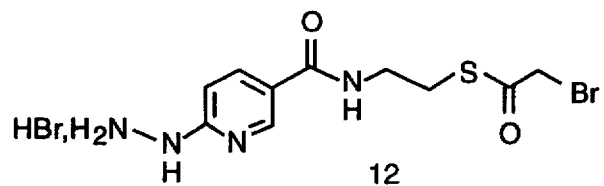
Figure 4K:
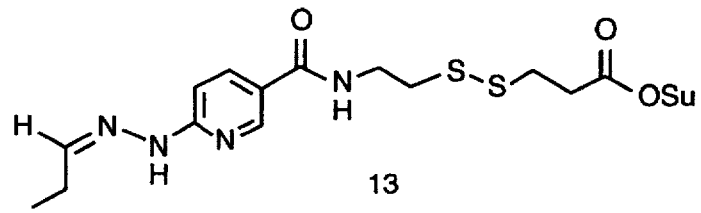
Figure 4L:
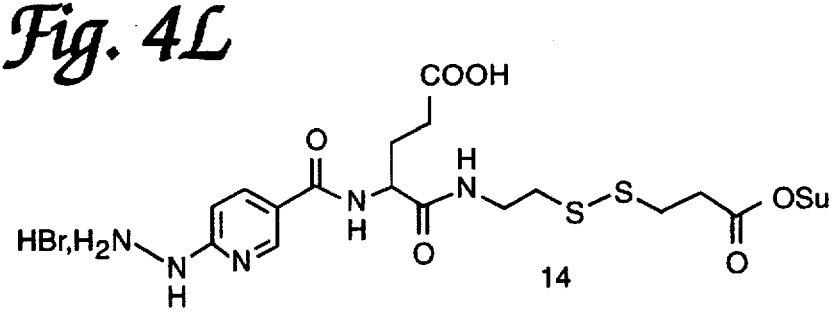
Figure 4M:
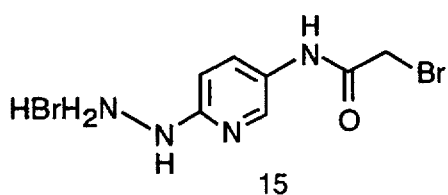
Figure 4N:
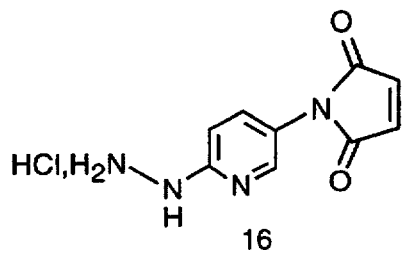
Figure 4O:
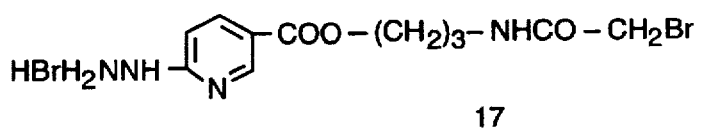
Figure 4P:
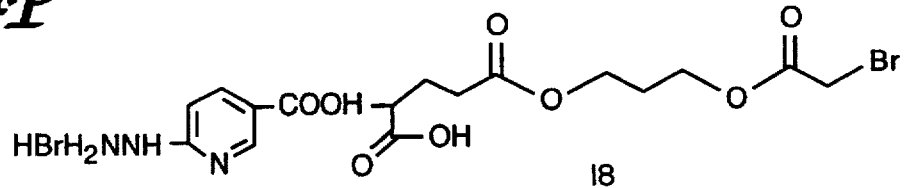

To a rapidly stirred solution of γ-t-butyl-(L)-glutamic acid (173 g) in a mixture of dioxane (5 ml) and saturated aqueous sodium bicarbonate solution (5 ml) was added succinimidyl (6-BOC-hydrazine)nicotinate (300 mg, 1.0 equiv) in one portion. The mixture was stirred for 3 hours then poured into water (50 ml). The pH was adjusted to pH 14 with 10N NaOH then to pH 7 with concentrated HCl and extracted once with ethyl acetate (40 ml). The pH of the aqueous phase was then lowered to pH 4 with concentrated HCl, saturated with sodium chloride and extracted with ethyl acetate (3×4 ml). The combined organic phases were dried (MgSO$_4$) and evaporated under reduced pressure giving the product as a white powder (360 mg, 96%).

6-(BOC-Hydrazine)nicotinamido-γ-t-butyl-(L)-glutamic Acid N-hydroxysuccinimidyl Ester To a stirred solution of 6-(BOC-hydrazine)nicotinamido-γ-t-butyl-(L)-glutamic acid (360 g) and N-hydroxysuccinimide (96 g) in THF (10 ml) under argon was added DCC (170 mg) at 0° C. The mixture was stirred at 0° C. for 2 hours then at room temperature overnight during which time a white solid had precipitated. The solid was filtered off and the filtrate evaporated under reduced pressure giving the product as a white foam (quant).

Synthesis of 1

6-Hydrazino-nicotinamido-(L)-glutamic Acid-N-hydroxy Succinimidyl Ester Hydrochloride To a stirred solution of 6-(BOC-hydrazine)nicotinamido-γ-t-butyl-(L)-glutamic acid-N-hydroxysuccinimidyl ester (150 mg) in dioxane (2 ml) was added a saturated solution of hydrogen chloride in dioxane (2 ml). After one hour a precipitate had formed from the homogeneous solution, stirring was continued for a further 3 hours, then the solid was filtered off, washed with ether and dried giving the produce as a white/yellow crystalline solid. $^1$H NMR (DMSO-$d_6$) δ2.10–2.29 (m, 2H, 2.39 (t, 2H, J=6.9 Hz), 2.81 (s, 4H), 4.88 (m, 1H, 6.93 (d, 1H, J=8.8 Hz), 8.18 (d, 1H, J=8.8 Hz), 8.63 (m, 2H), 9.04 (d, 1H, J=7.6 Hz, D$_2$O exchangeable), 9.95 (br.s, 2H, D$_2$O exchangeable); mass spectrum (FAB); m/e (relative intensity); 380 (60, M+1), 283(100), 201(35), 185(42), 136(40).

EXAMPLE 2

6-(BOC-Hydrazine)nicotinamido-γ-t-butyl-(L)-glutamyl-γ-benzyl-(L)-glutamic Acid t-Butyl Ester A solution of 6-(BOC-hydrazine)nicotinimido-γ-t-butyl-(L)-glutamic acid (200 mg), γ-benzyl-(L)-glutamic acid t-butyl ester hydrochloride (151 mg, 1.0 equiv) and N-hydroxysuccinimide (53 mg, 1.0 equiv) in DMF (10 ml) was cooled to 0° C. with stirring under argon. To this solution was added triethylamine (32 ml, 1.1 equiv) followed by DCC (94 mg, 1.0 equiv) in one portion and the mixture was stirred at 0° C. for 3 hours then at room temperature for 4 days during which time a white solid precipitated. The solution was diluted with ethyl acetate (50 ml), cooled, and the solid filtered off. The filtrate was evaporated to dryness under reduced pressure and the oily residue partitioned in ethyl acetate (50 ml) and saturated aqueous sodium bicarbonate solution (30 ml), the organic layer was separated, washed exhaustively with brine, dried (MgSO$_4$) and evaporated to dryness under reduced pressure giving a white foamy solid (90%).

6-(BOC-Hydrazine)nicotinamido-γ-t-butyl-(L)-glutamyl-(L)-glutamic Acid t-Butyl Ester To a suspension of palladium on activated carbon (Aldrich, 10%) in ethyl acetate (5 ml) was added 6-(BOC-hydrazine)nicotinamido-γ-t-butyl-(L)-glutamyl-γ-benzyl- (L)-glutamic acid t-butyl ester (300 mg) and the mixture was stirred rapidly under an atmosphere of hydrogen for 6 to 8 hours (until the reaction was complete by TLC). The mixture was filtered and evaporated to dryness under reduced pressure to give a white foam. This was used directly in the next step without further purification.

6-(BOC-Hydrazino)nicotinamido-γ-t-butyl-(L)-glutamyl-γ-N-hydroxysuccinimidyl-(L)-glutamic Acid t-Butyl Ester The product from above (100 mg) was dissolved in ethyl acetate (10 ml) with N-hydroxy succinimide (18.4 mg, 1.0 equiv) and cooled to 0° C. with stirring under argon. To this solution was added DCC (33 mg, 1.0 equiv) in one portion and the mixture was stirred overnight at room temperature during which time a white solid precipitated. The solid was filtered off and the filtrate evaporated to dryness under reduced pressure to give the product as a white foam.

Synthesis of 2

6-Hydrazine-nicotinamido-(L)-glutamyl-γ-N-hydroxysuccinimidyl-(L)-glutamic Acid Hydrochloride To a stirred solution of 6-(BOC-hydrazine)nicotinamido-γ-t-butyl-(L)-glutamyl-γN-hydroxy succinimidyl-(L)-glutamic acid t-butyl ester (20 mg) in dioxane (1 ml) was added a saturated solution of hydrogen chloride in dioxane (1 ml). After one hour a precipitate had formed from the homogeneous solution, stirring was continued for a further 24 hours, then the mixture evaporated to dryness under reduced pressure. The white/yellow solid which remained was washed with ether (3×) by decantation then evaporated and dried. $^1$H NMR (DMSO-d$_6$/D$_2$O) δ1.80–2.20 (m, 4H), 2.31 (m, 2H), 2.76 (m, 2H), 2.80 (s, 4H), 4.24 (m, 1H), 4.42 (m, 1H, 6.90 (d, 1H, J=8.8 Hz), 8.17 (dd, 1H, J=8.8, 2.4 Hz), 8.71 (s, 1H); mass spectrum (FAB); m/e relative intensity; 509 (18, M+1).

EXAMPLE 3

6-(2-Propenylhydrazone)nicotinamido-3-propanol

To a solution of succinimidyl 6-(2-propenylhydrazone) nicotinate (10 g, 34.4 mmol) in DMF (80 ml) was added a solution of 3-aminopropanol (3.0 ml, 37.9 mmol) in DMF (20 ml), dropwise and the mixture was stirred for 16 hours at room temperature then concentrated under reduced pressure. The residue, a pale yellow oil was dissolved in ethyl acetate (50 ml) and washed with the minimum amount of water, dried (Na$_2$SO$_4$) and concentrated under reduced pressure to a pale yellow solid which was recrystallised from ethyl acetate to give the desired product as a white solid (5.6 g, 65%).

N-Hydroxysuccinimidyl Glutaryl Chloride

Benkovic, Lerner WO 88 09380; An alternative one-pot procedure follows;

To a solution of glutaric acid anhydride (4.95 g) in dichloromethane (30 ml) was added N-hydroxy succinimide (5.0 g) in one portion and the mixture stirred for 2.5 hours at room temperature until the reaction was complete (checked by $^1$H NMR). To this mixture was added dropwise via a cannula oxalyl chloride (3.0 equiv, 2M solution in dichloromethane, Aldrich, 65 ml) during which time a strong effervescence occurred. The mixture was stirred overnight then evaporated to dryness under reduced pressure. Further dichloromethane was added and the mixture was evaporated once again. This procedure was repeated several times until the residue upon evaporation began to crystallise. The solid was washed with ether three times by decantation and dried giving the product as a white solid.

Synthesis of 3

To a solution of 6-(2-propenylhydrazone)nicotinamido-3-propanol (200 mg, 0.8 mmol) in THF (15 ml) under argon at 0° C. was added triethylamine (123 μl, 1.1 equiv) followed by N-hydroxy-succinimidylglutaryl chloride (200 mg, 0.8 mmol) in one portion and the mixture was allowed to warm to room temperature with stirring overnight. Evaporation under reduced pressure gave an oil which was re-dissolved in ethyl acetate and cooled in an ice bath giving a white crystalline precipitate of triethylamine hydrochloride which was filtered off. The filtrate was concentrated and purified by column chromatography and a short column of silica gel using 5% isopropanol in ethyl acetate as eluant. The desired product was obtained as a white powdered solid (80 mg, 22%). $^1$H NMR (CDCl$_3$) δ1.15 (t, 3H, J=7.5 Hz), 1.96 pentet, 2H, J=6.2 Hz), 2.08 (pentet, 2H, J=7.1 Hz), 2.31–2.40 (dq, 2H, J=7.5, 5.1 Hz), 2.51 (t, 2H, 7.1 Hz), 2.73 (t, 2H, J=7.1 Hz), 2.84 (s, 4H), 3.50 (q, 2H, J=6.4 Hz), 4.24 (t, 2H, J=6.1 Hz), 6.54 (br. t, 1H, D$_2$O exchangeable), 7.19–7.26 (m, 2H), 7.97–8.01 (dd, 1H, J=8.8, 2.4 Hz), 8.50 (dd, 1H, J=2.4, 0.7 Hz); mass spectrum (FAB); m/e (relative intensity); 462 (100, M+1), 432 (10), 233 (42).

EXAMPLE 4

3-Hydroxypropyl-[6-(2-propenylhydrazone)] nicotinate

To a mixture of 6-(2-propenylhydrazone)nicotinic acid (3.08 g, 15.5 mmol) and potassium carbonate (5.4 g, 39 mmol) in DMF (20 ml) was added 3-bromo-1-propanol (2.58 g, 18.6 mmol). The reaction mixture was stirred under argon at 70° C. for 16 hours. The solution was cooled and concentrated to dryness under reduced pressure. The residue was dissolved in ethyl acetate (100 ml) and extracted with water (2×50 ml). The organic phase was dried (Na$_2$SO$_4$) and evaporated under reduced pressure to give a reddish solid. Column chromatography (silica gel; methylene chloride/methanol (95/5) was used to isolate the product as a white solid (2.3 g, 60%).

Synthesis of 4

[3-Pyridinecarboxylic Acid, 6-Propylidenehydrazino)-3-[(bromoacetyl)oxy]propyl Ester]

To a stirred solution of 3-hydroxypropyl-[6-(2-propenylhydrazone)]nicotinate (150 mg, 0.6 mmol) and anhydrous sodium carbonate (127 mg, 1.20 mmol) in dry methylene chloride (20 ml), under argon, was added bromoacetyl bromide (112 mg, 0.60 mmol) dropwise at 0°–5° C. The reaction mixture was stirred at 0°–5° C. for 1 hour then at room temperature for 1 hour. The solid was filtered off and the filtrate after dilution with methylene chloride (50 ml) was extracted with water (25 ml). The organic phase was dried (Na$_2$SO$_4$) and evaporated under reduced pressure giving the crude product as a gummy solid. Preparative TLC (Silica gel plate 1000 μm, ethyl acetate/hexane (2/1)) was used to isolate the product as a white solid (120 mg, 54%). $^1$H NMR (CDCl$_3$) δ1.16 (t, 3H, J=7.5 Hz), 2.15 (m, 2H, J=6.3 Hz), 2.36 (m, 2H, J=7.6 Hz), 3.84 (s, 2H), 4.34 (t, 2H, J=6.2 Hz), 4.41 (t, 2H, J=6.3 Hz), 7.31 (e, 1H, J=10.4 Hz), 7.33 (t, 1H), 8.18 (dd, 1H, J=2.2, 9.1 Hz), 8.66 (d, J=2.2 Hz); mass spectrum (TAB); m/e relative intensity); 374 (100, M+1), 372 (100, M+1), 294 (25), 176 (52), 121 (46).

EXAMPLE 5

S-(2-thiopyridyl)-(L)-cysteine Hydrochloride

This disulphide was synthesised by the method of P. C. S. Chong and R. S. Hodges, J. Biol. Chem., (1981), 256, 5064.

6-(BOC-Hydrazino)nicotinamido-[S-(2-thiopyridyl)]-(L)-cysteine

To a solution of S-(2-thiopyridyl)-(L)-cysteine hydrochloride (369 mg, 1.37 mmol) and saturated aqueous sodium bicarbonate solution (5 ml) and water (3 ml) was added a solution of succinimidyl 6-(BOC-hydrazino)pyridine-5-carboxylate (500 mg, 1.42 mmol) in dioxane (5 ml). The reaction mixture was stirred at room temperature for 2.5 hours. Water (25 ml) was added to the reaction mixture and the aqueous solution was washed with ethyl acetate to remove unreacted ester. The aqueous phase was saturated with sodium chloride and acidified to pH 3.7. The aqueous solution was extracted with ethyl acetate (2×25 ml). The combined organic extracts were dried over magnesium sulphate, filtered and concentrated to give 611 mg of a sticky white solid. Ether was added to the flask and the solids scraped from the sides and isolated by filtration to give the desired product as a white solid (550 mg, 82%).

Synthesis of 5

6-Hydrazino-nicotinamido-S-(2-thiopyridyl)-(L)-cysteine Hydrochloride

A solution of hydrogen chloride (gas) in dry dioxane was prepared by bubbling hydrogen chloride into dry dioxane at a moderate rate for 5 minutes. To the hydrogen chloride/dioxane solution (5 ml) was added 6-(BOC-hydrazino) nicotinamido-[S-(2-thiopyridyl)]-(L)-cysteine (50 mg). The reaction mixture was stirred at room temperature for 2 hours and a white precipitate formed. The solvent was removed under reduced pressure and subsequently dried under high vacuum to give 35 mg of a white amorphous solid. $^1$H NMR $\delta$3.30 (m, 2H, 4.65 (m, 1H), 6.93 (d, 1H, J=8.6 Hz), 7.25 (m, 1H), 7.75 (m, 1H), 8.15 (d, 1H, J=8.6 Hz), 8.45 (d, 1H), 8.70 (s, 1H), 9.05 (d, 1H); mass spectrum (FAB); m/e; 366, 351, 257, 223, 202, 179.

EXAMPLE 6

S-(2-Thio-5-nitropyridyl)-(L)-cysteine Hydrochloride

4-Nitropyridine disulphide (1.98 g, 6.34 mmol) was added to DMF (10 ml) and the mixture was heated to aid dissolution. The solution was cooled to room temperature and a solution of (L)-cysteine hydrochloride (0.5 g, 3.17 mmol) in DMF (6 ml) was added. The reaction mixture became bright yellow and was stirred at room temperature for 16 hours. A minor amount of precipitate formed which was removed by filtration. The filtrate was concentrated to give a thick yellow-brown oil which on treatment with dichloromethane yielded a yellow precipitate. The precipitate was isolated by filtration. The solids were dissolved in methanol with mild heating and filtered to remove white insoluble solids. The filtrate was treated with ether to induce precipitation. The yellow solid was isolated by filtration to give 240 mg of the desired product. A further 120 mg of product precipitated from the original dichloromethane filtrate; total yield 360 mg (39%).

6-(BOC-Hydrazine)nicotinamido-S-(2-thio-5-nitropyridyl)-(L)-cysteine

S-(2-Thio-5-nitropyridyl)-(L)-cysteine hydrochloride (220 mg, 0.70 mmol) was dissolved in saturated aqueous sodium bicarbonate (5 ml) and a solution of succinimidyl 6-(BOC-hydrazino)nicotinate (246 g, 0.70 mmol) in dioxane (5 ml) was added and the reaction mixture was stirred at room temperature for 3 hours. Water (25 ml) was added and the aqueous solution was washed with ethyl acetate to remove unreacted ester. The aqueous phase was acidified to pH 3.3 with 1N HCl then saturated with sodium chloride. The acidic aqueous solution was extracted with ethyl acetate (2×35 ml). The combined organic extracts were dried over magnesium sulphate, filtered and concentrated to give 145 mg of a yellow solid which was suspended in ether and isolated by filtration to give 35 mg of the desired product. The filtrate was concentrated and treated with ether/hexanes to yield a further 95 mg of desired product; total yield 125 mg (35%).

Synthesis of 6

6-(Hydrazino-nicotinamido-S-(2-thio-5-nitropyridyl)-(L)-cysteine Hydrochloride

A solution of hydrogen chloride (gas) in dry dioxane was prepared by bubbling hydrogen chloride into dry dioxane at a moderate rate for 5 minutes. To a hydrogen chloride/dioxane solution (5 ml) was added 6-(BOC-hydrazino) nicotinamido-S-(2-thio-5-nitro-pyridyl)-(L)-cysteine (50 mg). The reaction mixture was stirred at room temperature for 2 hours and a white precipitate formed. The solvent was removed under reduced pressure and subsequently dried under high vacuum to give 25 mg of a white amorphous solid. $^1$H NMR $\delta$3.30 (m, 2H), 4.66 (m, 1H), 6.92 (d, 1H, J=9.0 Hz), 8.01 (d, 1H, J=9.0 Hz), 8.12 (d, 1H, J=8.9 Hz), 8.48 (dd, 1H, J=8.9, 2.7 Hz), 8.64 (s, 1H), 9.03 (d, 1H, J=8.3 Hz), 9.2 (br. s, 1H); mass spectrum (FAB); m/e; 411, 391, 363, 335, 307, 293, 277, 257, 201, 185, 171, 157.

EXAMPLE 7

Synthesis of 7

Prepared from (L)-penicillamine using similar experimental procedures to those described in Examples 5 and 6. $^1$H NMR (DMSO-d$_6$) $\delta$1.41 (s, 3H), 1.43 (s, 3H), 4.75 (m, 1H), 6.92 (d, 1H, J=9.1 Hz), 7.20 (m, 1H), 7.79 (m, 2H), 8.14 (dd, 1H, J=9.8, 2.3 Hz), 8.39 (d, 1H, J=4.0 Hz), 8.54 (s, 1H); mass spectrum (FAB); m/e (relative intensity); 394 (100, M+1).

EXAMPLE 8

6-(BOC-Hydrazino)nicotinamido-3-propanol

To a stirred solution of succinimidyl 6-(BOC-hydrazino)-nicotinate (350 mg) in DMF (4 ml) cooled to 0°–5° C. was added a solution of 3-amino-1-propanol (90 mg, 1.2 equiv) in DMF (2 ml). The mixture was stirred at 0°–5° C. for 1 hour and then at room temperature for 16 hours. The reaction mixture was concentrated to dryness to give a white solid residue. The residue was dissolved in ethyl acetate (100 ml) and extracted with water (2×25 ml). The organic phase was dried (Na$_2$SO$_4$) and evaporated under reduced pressure giving the product as a white powder (330 mg, 90%).

To a stirred solution of 6-(BOC-hydrazino)nicotinamido-3-propanol (296 mg, 1 equiv) and anhydrous sodium carbonate (212 mg, 2 equiv) in dry methylene chloride (15 ml), under argon, was added bromoacetyl bromide (200 mg, 1.1 equiv) dropwise at 0°–5° C. The mixture was stirred at 0°–5° C. for ½ hour then at room temperature for 2 hours. The solid was filtered off and the filtrate after dilution with methylene chloride (50 ml) was extracted with water (25 ml). The organic phase was dried (Na$_2$SO$_4$) and evaporated under reduced pressure giving the crude product as a pale yellow solid. The crude product was purified by column chromatography on silica gel using methylene chloride/methanol (90/10) as the eluent, giving the pure bromoacetylated product as a white solid (267 mg, 62%) was obtained.

Synthesis of 8

[Acetic Acid, Bromo-, 3-[[(6-Hydrazino-3-pyridinyl)carbonyl]amino]propyo Ester Monohydrobromine)]

A solution of hydrogen bromide in ethyl acetate was prepared by passing anhydrous hydrogen bromide (gas) through ethyl acetate (10 ml) at a moderate rate for 5 minutes.

The above bromoacetate (90 mg) was dissolved in ethyl acetate (1 ml) and HBr/ethyl acetate (2 ml) was added and the reaction mixture was stirred at room temperature. After 5 minutes the solution became cloudy and a precipitate formed. Stirring was continued for 2½ hours. The cloudy mixture was filtered, washed with ether (3×10 ml) and dried under reduced pressure to yield a white solid (65 mg, 71%). $^1$H NMR (DMSO-d$_6$) δ1.95 (t, 2H, J=6.2 Hz), 3.35 (t, 2H, J32 6.2 Hz), 4.15 (s, 2H), 4.20 (t, 2H, J=6.2 Hz), 6.95 (d, 1H, J=8.8 Hz), 8.15 (dd, 1H, J=2.4, 8.8 Hz), 8.65 (d, 1H, J=2.4 Hz); mass spectrum (FAB); m/e (relative intensity); 333 (33, M+1), 331 (33, M+1), 136 (100).

EXAMPLE 9

3-Hydroxypropyl 6-(BOC-hydrazino)nicotinate

To a mixture of 6-(BOC-hydrazino)nicotinic acid (3.0 g, 11.86 mmol) and potassium carbonate (2.2 g, 15.9 mmol) in DMF (20 ml) was added 3-bromo-1-propanol (2.0 g, 14.39 mmol). The reaction mixture was stirred under argon at 70° C. for 16 hours. The solution was cooled and concentrated to dryness under reduced pressure. The brown residue was dissolved in ethyl acetate (100 ml) and extracted with water (2×50 ml). The organic phase was dried (Na$_2$SO$_4$) and evaporated under reduced pressure to give a pale yellow oil. Column chromatography (silica gel, ethyl acetate/hexane (3/1)) was used to isolate the product as a white solid (2.28 g, 60%).

To a stirred solution of the above ester-alcohol (935 mg, 3.0 mmol) and anhydrous sodium carbonate (636 mg, 6.0 mmol) in dry methylene chloride (25 ml), under argon, was added bromoacetyl bromide (290 μl, 3.6 mmol) dropwise at 0°–5° C. The reaction mixture was stirred at 0°–5° C. for 30 minutes then at room temperature for 1 hour. The solid was filtered off and the filtrate after dilution with methylene chloride (50 ml) was extracted with water (25 ml). The organic phase was dried (Na$_2$SO$_4$) and evaporated under reduced pressure giving the crude product as a brownish yellow sticky solid. Column chromatography (silica gel; ethyl acetate/hexane (2/1)) was used to isolate the pure product as a white solid (0.36 g, 28%).

Synthesis of 9

A solution of hydrogen bromide in dioxane was prepared by passing anhydrous hydrogen bromide (gas) into dioxane (10 ml) at a moderate rate for 5 minute. The above bromoacetate (75 mg) was dissolved in dioxane (2 ml) and HBr/dioxane (2 ml) was added and the reaction mixture was stirred at room temperature for 2 minutes. The cloudy mixture was filtered, washed with ether (3×10 ml) and dried under reduced pressure to yield a white solid (40 mg, 56%). $^1$H NMR (D$_2$O) δ2.18 (t, 2H, J=6.0 Hz), 4.01 (s, 2H), 4.39 (t, 2H, J=6.0 Hz), 4.44 (t, 2H, J=6.0 Hz), 6.89 (d, 1H, J=9.0 Hz), 8.13 (dd, 1H, J=2.0, 9.2 Hz), 8.62 (d, 1H, J=2.0 Hz); mass spectrum (FAB); m/e (relative intensity); 334 (100, M+1), 332 (100, M+1), 212 (76), 194 (38), 154 (48), 136 (45).

EXAMPLE 10

3-Hydroxypropyl[(6-BOC-hydrazino)nicotinamido]-γ-t-butyl-(L)-glutamate

To a stirred solution of 6-(BOC-hydrazino)nicotinamido-γ-t-butyl-(L)-glutamic acid (1.0 g, 2.29 mmol) and potassium carbonate (348 mg, 1.1 equiv) in DMF (5 ml) was added 3-bromopropanol (227 μl, 1.1 equiv) and the mixture was heated at 55°–60° C. overnight. The solution was evaporated to dryness under reduced pressure and the residue partitioned between ethyl acetate and saturated aqueous sodium bicarbonate. The organic phase was separated and washed exhaustively with water, dried (Na$_2$SO$_4$) and evaporated under reduced pressure giving a foamy white solid. The desired product was purified by column chromatography on silica gel using 90% ethylacetate in hexane as eluent, giving a white solid (900 mg, 78%).

The compound from above (200 mg, 0.40 mmol) and anhydrous sodium carbonate (84 mg, 2.0 equiv) were dissolved in dichloromethane (10 ml) and cooled to 0° C. under argon. Bromoacetylbromide (40 μl, 1.2 equiv) was added dropwise and the mixture was allowed to warm to room temperature overnight. Ethyl acetate (20 ml) was added and the solution washed with saturated aqueous sodium bicarbonate, dried (Na$_2$SO$_4$) and evaporated under reduced pressure. The desired product was purified by column chromatography on silica gel using 80% ethyl acetate in hexane as eluent to give a colourless oil (40 mg, 16%).

Synthesis of 10

The bromoacetate described above (40 mg, 0.06 mmol) was dissolved in anhydrous dioxane and cooled in an ice bath. Hydrogen bromide (gas) was passed through the solution for approximately 1 minute (or until saturated). The solution was allowed to stand at 0° C. for 3 minutes then ether was added to precipitate the product. The white solid was allowed to settle to the bottom of the flask and the supernatant hydrogen bromide solution was decanted off with a pasteur pipette. The solid was then washed by decantation with ether ten times and the remaining traces of ether removed by evaporation under reduced pressure and drying in vacuo overnight. The product was a white solid (25 mg, 77%). $^1$H NMR (D$_2$O) δ2.07 (pentet, 2H, J=6.2 Hz), 2.09–2.31 (m, 2H), 2.38 (t, 2H, J=6.9 Hz), 4.02 (s, 2H, 4.25 (t, 2H, J=6.1 Hz, 4.31 (t, 2H, J=5.9 Hz), 4.53 (m, 1H, 6.96 (d, 1H, J=9.3 Hz), 8.06–8.09 (dd, 1H, J=9.3, 2.1 Hz), 8.41 (d, 1H, J=2.0 Hz); mass spectrum (FAB); m/e (relative intensity); 463 (100, M+1), 461 (100, M+1), 383 (22), 339 (10), 237 (10).

EXAMPLE 11

2-Carboxyethyl-2-pyridyldisulphide was prepared by the procedure according to Carlesson et al., Biochem. J. (1978), 173, 723–737.

Synthesis of 11

To a stirred solution of 6-(2-propenylhydrazone)nicotinamido-3-propanol (190 mg, 0.8 mmol) and 2-carboxyethyl-2-pyridyldisulphide (163 mg, 1.0 equiv) in THF (10 ml) at 0° C. was added dicyclohexyl-carbodiimide (157 mg, 1.0 equiv) and the mixture was stirred at 0°–5° C. for 72 hours during which time a white solid precipitated. The white solid was filtered off and the filtrate evaporated under reduced pressure. The residue was dissolved in ethyl acetate and cooled, which gave a further precipitate of dicyclohexyl urea ("DCU"). This procedure was repeated once again until all of the urea had been removed. The desired product was purified by column chromatography on silica gel using 5% methanol in dichloromethane as eluent. Re-crystallisation in ethyl acetate/ether gave white solid (85 mg, 25%). $^1$H NMR (CDCl$_3$) δ1.15 (t, 3H, J=7.5 Hz), 1.95 (pentet, 2H, J=6.0 Hz), 2.36 (dq, 2H, J=5.0, 7.6 Hz), 2.80 (t, 2H, J=7.0 Hz), 3.07 (t, 2H, J=7.0 Hz), 3.50 (m, 2H), 4.04 (t, 2H, J=6.0 Hz), 6.51 (broad triplet, 1H, D$_2$O exchangeable), 7.07–7.12 (m, 1H, 7.17–7.21 (m, 2H), 7.60–7.72 (m, 2H), 7.95–7.99 (dd, 1H, J=8.8, 2.4 Hz), 8.22 (broad s, 1H, D$_2$O exchangeable), 8.42–8.45 (m, 1H), 8.55 (d, 1H, J32 2.4 Hz); mass spectrum (FAB); m/e relative intensity); 448 (100, M+1), 176 (45).

EXAMPLE 12

6-(BOC hydrazino)nicotinamido-2-ethanethiol

To a stirred solution of succinimidyl 6-(BOC-hydrazino)-nicotinate (2.0 g, 5.7 mmol) and triethylamine (0.8 ml, 5.7 mmol) in DMF (20 ml) was added 2-aminoethanethiol hydrochloride (0.65 g, 5.7). The reaction mixture was stirred at room temperature for 16 hours. The solution was concentrated to dryness under reduced pressure. The residue was dissolved in ethyl acetate (100 ml) and extracted with water (50 ml). The organic phase was dried (Na$_2$SO$_4$) and evaporated under reduced pressure giving the product as a white powder (1.19 g, 67%).

To a stirred solution of 6-(BOC hydrazino)nicotinamido-2-ethanethiol (200 mg) and anhydrous sodium carbonate (2 equiv) in dry methylene chloride (20 ml), under argon, was added bromoacetyl bromide (1.2 equiv) dropwise at 0°–5° C. The reaction mixture was stirred at 0°–5° C. for 30 minutes, then at room temperature for 1 hour. The solids were filtered off and the filtrate after dilution with methylene chloride (50 ml) was extracted with water (25 ml). The organic phase was dried (Na$_2$SO$_4$) and evaporated under reduced pressure giving the crude product as a light brown solid. Column chromatography (silica gel; ethyl acetate/hexane (2/1)) was used to isolate the pure product as a pale yellow solid (110 mg, 41%).

Synthesis of 12

[Acetic Acid, Bromo, 2-[[(6-Hydrazino-3-pyridinyl)carbonyl]amino]ethyl Thioester, Monohydrobromide]

A solution of hydrogen bromide in ethyl acetate was prepared by passing anhydrous hydrogen bromide into ethyl acetate (10 ml) at a moderate rate for 5 minutes. The above BOC-hydrazinopyridine derivative (22 mg) was dissolved in ethyl acetate (1 ml) and HBr/ethyl acetate (2 ml) was added and the reaction mixture was stirred at room temperature for 1 hour. The cloudy reaction mixture was filtered to give 12 mg of a white solid (57%). $^1$H NMR DMSO-d$_6$) δ3.15 (t, 2H), 3.45 (m, 2H), 4.45 (s, 2H), 6.95 (d, 1H), 8.15 (d, H), 8.65 (s, 1H); mass spectrum (FAB); m/e (relative intensity); 335 (42, M+1), 333 (42, M+1), 185 (100).

EXAMPLE 13

S-(2-Pyridyl)-S'(2-aminoethyl Disulphide Hydrochloride

To a stirred solution of Aldrithiol (8.8 g, 0.04 mol) and glacial acetic acid (1.6 ml) in methanol (40 ml) was added dropwise 2-aminoethanethiol hydrochloride (2.3 g, 0.02 mol) in methanol (25 ml). The bright yellow solution was stirred at room temperature for 16 hours. The solution was concentrated to dryness under reduced pressure. The residue was stirred with methylene chloride (100 ml) and filtered giving the product as a white powder (3.6 g, 80%).

6-(2-Propenylhydrazone)-N-(2'-pyridyldithioethyl) nicotinamide (Compound of Formula II)

To a solution of succinimidyl 6-(2-propenylhydrazone)nicotinate (590 mg, 2.0 mmol) and triethylamine (0.6 ml) in DMF (20 ml) was added 2-pyridyl dithioaminoethane hydrochloride (444 mg, 2 mmol). The reaction mixture was stirred at room temperature for 16 hours. The solution was concentrated to dryness under reduced pressure. The residue was dissolved in ethyl acetate (100 ml) and extracted with water (2×50 ml). The organic phase was dried (Na$_2$SO$_4$) and evaporated under reduced pressure giving the produce as a white powder (650 mg, 90%). $^1$H NMR (DMSO-d6) δ1.02 (t, 3H, 2.25 (q, 2H), 3.05 (t, 2H), 3.55 (m, 2H), 7.05 (d, 1H), 7.25 (m, 1H, 7.45 (t, 1H), 7.85 (m, 2H, 7.95 (d, 1H), 7.55 (m, 3H).

To a solution of the above disulphide (361 mg, 1.00 mmol) and glacial acetic acid (20 µl) in DMF (10 ml) was added dropwise mercaptopropionic acid (106 mg, 1.0 mmol) in DMF (2 ml). The reaction mixture was stirred at room temperature for 16 hours. The solution was concentrated to dryness under reduced pressure. The residue was triturated with methylene chloride (10 ml) and filtered giving the product as a white powder (208 mg, 58%).

Synthesis of 13

To a stirred solution of the above acid (108 mg, 0.30 mmol) and N-hydroxysuccinimide (35 mg; 0.30 mmol) in DMF (5 ml) was added DCC (63 mg, 0.31 mmol) at 0° C. The mixture was stirred at 4° C. for 16 hours. The white solid (DCU) was filtered off and the filtrate concentrated to dryness under reduced pressure. The residue was triturated with ethyl acetate (25 ml) and filtered. The filtrate was concentrated under reduced pressure giving 13 as a white powder (70 mg, 51%). $^1$H NMR (CDCl$_3$) δ1.15 (t, 3H, J=7.5 Hz), 2.35 (m, 2H, J=7.5 Hz), 2.91 (s, 4H), 2.94 (t, 2H, J=6.7 Hz), 3.03 (m, 2H, 3.11 (m, 2H), 3.75 (q, 2H, J=6.4 Hz), 7.17 (d, 1H, J=7.95 HZ), 7.21 (t, 1H, J=4.7 Hz), 7.98 (dd, 1H, J=2.4, 8.8 Hz), 8.53 (d, 1H); mass spectrum (FAB); m/e (relative intensity); 454 (100, M+1), 253 (32), 225 (82), 176 (61), 121 (46).

EXAMPLE 14

To a stirred solution of 6-(BOC-hydrazino)nicotinamido-t-butyl-(L)-glutamic acid (1 g, 2.3 mmol), triethylamine (0.32 ml, 2.3 mmol) and S-(2-pyridyl)-S'-(2-aminoethyl) disulphide (507 mg, 2.3 mmol) in DMF (10 ml) was added DCC (472 mg, 2.3 mmol) at 0° C. The mixture was stirred at 4° C. for 16 hours. The precipitated solid (DCU) was filtered and the solution concentrated to dryness under reduced pressure. The residue was dissolved in ethyl acetate (100 ml) and extracted with saturated sodium bicarbonate (50 ml), brine (50 ml and water (50 ml). The organic phase was dried ($Na_2SO_4$) and evaporated under reduced pressure giving the product as a white solid (1.28 g, 92%).

To a solution of the above BOC-hydrazinopyridylglutamyl disulphide (606 mg, 1.0 mmol) and glacial acetic acid (100 µl) in ethanol (25 ml) was added dropwise 3-mercaptopropionic acid (106 mg, 1.0 mmol) in ethanol (10 ml). The reaction mixture was stirred at room temperature for 16 hours. The solution was concentrated to dryness under reduced pressure to a yellow solid. Column chromatography (silica gel; methylene chloride/methanol (3/2) and acetic acid (4% of the eluate)) was used to isolate the product as a white solid (302 mg, 50%).

To a stirred solution of BOC-hydrazinopyridinedisulphide acid (170 mg, 0.28 mmol) and N-hydroxysuccinimide (33 mg, 0.29 mmol) in DMF (5 ml) was added DCC (58.4 mg, 0.28 mmol) at 0° C. The reaction mixture was stirred at 4°0 C. for 16 hours. The white solid (DCU) was filtered off and the filtrate concentrated to dryness under reduced pressure. The residue was triturated with ethyl acetate (25 ml) and filtered. The filtrate was concentrated under reduced pressure giving the product as a white powder (75 mg, 38%).

Synthesis of 14

A solution of hydrogen bromide in ethyl acetate was prepared by passing anhydrous hydrogen bromide (gas) into ethyl acetate (10 ml) at a moderate rate for 5 minutes. 6-BOC-Hydrazinoglutamyl-disulphide (30 mg) was dissolved in ethyl acetate (1 ml) and HBr/ethyl acetate (1 ml) was added and the reaction mixture was stirred at room temperature for 20 minutes. The slurry was filtered and dried to give a white solid (21 mg, 78%). $^1$H NMR ($CD_3OD$) δ2.15 (m, 2H), 2.45 (t, 2H, 2.83 (s, 4H), 2.88 (m, 2H, 3.05 (m, 4H), 3.45 (m, 2H, 4.45 (m, 1H), 6.95 (d, 1H, 8.25 (d, 1H), 8.45 (s, 1H); mass spectrum (FAB); m/e (relative intensity); 543 (22, M+1), 322 (49), 269 (100), 207 (85).

To permit comparison in biological testing, the following compounds were prepared:

6-(BOC-Hydrazino)-3-(N-bromoacetyl) aminopyridine

To a stirred solution of 3-amino-6-(BOC hydrazino) pyridine (1.2 g, 5.4 mmol) and anhydrous sodium carbonate (682 mg, 6.4 mmol) in dry acetonitrile (25 ml), under argon, was added bromoacetyl chloride (1.1 g, 6.4 mmol) dropwise at 0°–5° C. The mixture was stirred at 0.5° C. for ½ hour then at room temperature for 3 hours.

The reaction mixture was concentrated under reduced pressure and the residue was partitioned between water (50 ml) and ethyl acetate (150 ml). The organic phase was separated, dried ($Na_2SO_4$) and concentrated under reduced pressure to 25–30 ml. The white solid (1.0 g, 54.3%) which precipitated out was filtered and dried. $^1$H NMR (DMSO-$d_6$): δ1.39 (s, 9H); 3.99 (s, 2H); 6.45 (d, 1H, J=8.8 Hz); 7.65 (dd, 1H, J=2.4, 8.8 Hz); 8.15 (d, 1H, J=2.4 Hz). Analysis: Calculated for $C_{12}H_{17}N_4BrO_3$: C—41.75; H—4.96; N—16.23; Br—23.15. Found: C—41.87; H—5.00; N—16.27; Br—23.27.

3-(N-Bromoacetyl)amino-6-hydrazinopyridine Hydrobromide (Compound 15)

A solution of hydrogen bromide in dioxane was prepared by bubbling anhydrous hydrogen bromide (gas) through dioxane (10 ml) at a moderate rate for 5 minutes. 6-(BOC-hydrazino)-3-(N-bromoacetyl)aminopyridine (60 mg) was dissolved in dioxane (2 ml) and HBr/dioxane (2 ml) was added and the reaction mixture was stirred at room temperature for 30 minutes during which time a precipitate had formed. The reaction mixture was stirred at room temperature for a total of 4 hours, then filtered, washed with ether (3×25 ml) and dried under reduced pressure to give a while solid (50 mg, 87.7%). $^1$H NMR ($D_2O$): δ4.08 (s, 2H); 7.02 (d, 1H, J=8.8 Hz); 7.85 (dd, 1H, J=2.4, 8.8 Hz); 8.25 (d, 1H, J=2.4 Hz).

Following the synthetic procedures described in European Patent Application No EP 0 384 769 A2, 3-amino-6-(BOC-hydrazino)-pyridine was used to prepare 3-maleimido-6-hydrazinopyridine hydrochloride (Compound 16).

Additional novel compounds according to the invention have been prepared:

EXAMPLE 17

3-(Benzyloxyacetylamido)-1-propanol

To a stirred solution of 3-amino-1-propanol (3.0 g, 68.83 mmol), sodium bicarbonate, (14.5 g, 172.6 mmol), water (100 ml), and dioxane (52 ml) was added a solution of benzyloxyacetyl chloride (19.5 g, 106.0 mmol) in dioxane (36 ml), dropwise at 0.5° C. for 4 hours. The mixture was extracted with ethyl acetate (3×200 ml) and the combined organic phases were washed with brine, dried ($MgSO_4$) and evaporated under reduced pressure giving the product as a clear oil (11.1 g, 72%).

3-(Benzyloxyacetylamido)-1-propyl-(6-BOC-hydrazino)nicotinate

To a stirred solution of 6-(BOC-hydrazino)nicotinic acid (5.0 g, 19.74 mmol), DMF (25 ml), 3-benzyloxyacetylamido)-1-propanol (4.4 g, 19.74 mmol) and 4-(dimethylamino)pyridine (2.48 g, 19.74 mmol) was added a solution of DCC (4.48 g, 21.71 mmol) in DMF (10 ml) dropwise at 0° C. and the mixture was stirred for 16 hours. The solution was diluted with ethyl acetate (250 ml), cooled and the solid filtered off. The filtrate was evaporated to dryness under reduced pressure and the oily residue partitioned in ethyl acetate (200 ml) and saturated sodium bicarbonate solution (30 ml). The organic layer was separated, dried ($MgSO_4$) and evaporated under reduced pressure. The product was purified by column chromatography (silica gel: ethyl acetate) to give a white solid (5.1 g, 56%).

3-Hydroxyacetylamido)-1-propyl-6-(BOC-hydrazino)nicotinate

To a suspension of palladium on activated carbon (Aldrich 10%, 1.0 g) in methanol (16 ml) was added 3-benzyloxyacetylamido)-1-propyl-(6-BOC-hydrazino) nicotinate (1.6 g, 3.48 mmol) and ammonium formate (1.1 g, 17.44 mmol). The mixture was stirred rapidly under argon for 16 hours. The suspension was filtered through celite and evaporated under reduced pressure to give a white foam (1.0 g, 78%).

3-Methanesulphonyloxyacetylamido)-1-propyl-(6-BOC-hydrazino)nicotinate

To a stirred solution of 3-hydroxyacetylamido)-1-propyl-(6-BOC-hydrazino)nicotinate (1.0 g, 2.17 mmol) and triethylamine (0.41 ml, 2.98 mmol) in dichloromethane (20 ml) was added a solution of methanesulphonyl chloride (0.23 ml, 2.98 mmol) in dichloromethane (5 ml) dropwise at 0° C. and the reaction mixture was then allowed to stir at 0° C. for a further 2 hours then evaporated under reduced pressure. The residue was dissolved in ethyl acetate and washed with water, dried (MgSO$_4$) and evaporated under reduced pressure to give a white foam (1.2 g, 98%).

3-(Bromoacetylamido)-1-propyl-(6-BOC-hydrazino) nicotinate

To a stirred solution of 3-methanesulphonyl-oxyacetylamido)-1-propyl-(6-BOC-hydrazino)nicotinate (1.2 g, 2.68 mmol) in acetone (20 ml) was added a solution of lithium bromide (1.7 g, 26.9 mmol) in acetone (30 ml) dropwise and the reaction mixture was heated to reflux for 1.5 hours. After allowing to cool to room temperature the mixture was evaporated under reduced pressure and the residue was dissolved in ethyl acetate (100 ml) and washed with water (3×100 ml). The organic layer was separated, dried (MgSO$_4$) and evaporated under reduced pressure and the product was purified by column chromatography (silica gel: ethyl acetate) to give a white foam (0.8 g, 69%). $^1$H NMR (CDCl$_3$) δ1.47 (s, 9H), 2.00 (pentet, 2H, J=6.2 Hz), 3.43 (q, 2H, J=6.3 Hz), 3.89 (s, 2H), 4.39 (t, 2H, J=5.9 Hz), 6.73 (d, 1H, J32 8.8 Hz), 8.15 (dd, 1H, J=2.2 Hz, 8.7 Hz), 8.82 (d, H, J=2.2 Hz).

3-(Bromoacetylamido-1-propyl-(6-hydrazino) nicotinate Monohydrobromide

To a stirred solution of 3-(bromoacetylamido)-1-propyl-(6-BOC-hydrazino)nicotinate (50 mg) and acetic acid (1 ml) under argon was added hydrogen bromide (Aldrich, 30 wt % solution in acetic acid, 1 ml). The reaction mixture was stirred for 3 minutes and ether (20 ml) was added immediately to precipitate the product. After stirring for 1 minute, the ether was decanted off. The product was repeatedly washed with ether (6–10 times) and the final traces were removed by evaporating under reduced pressure to give a white solid (18 mg, 37%). $^1$H NMR (DMSO-d$_6$) δ1.86 (pentet, 2H, J=6.5 Hx), 3.22 (q, 2H, J=6.5 Hz), 3.83 (s, 2H), 4.25 (t, 2H, J=6.2 Hz), 6.91 (d, 1H, J=8.8 Hz, 8.14 (dd, 1H, J=2.2 Hz, 8.8 Hz), 8.40 Br.t, 1H, D$_2$O exchangeable), 8.69 (d, 1H, J=8.8 Hz); mass spectrum (FAB); m/e (relative intensity); 333 (100, M+1), 331 (100, M+1), 253 (15), 194 (43), 178 (20).

EXAMPLE 18

Using the procedure described in Example 1, α-t-butyl-(L)-glutamic acid gave 6-BOC-hydrazino)nicotinamide-α-t-butyl-(L)-glutamic acid. Using the procedure in Example 10, 6-BOC-hydrazino)nicotinamide-α-t-butyl-(L)-glutamic acid was converted to the γ-bromoacetate derived glutamic acid linker molecule.

Final De-protection Procedure to a stirred solution of the bromoacetate (100 mg, 0.162 mmol) in acetic acid (2 ml) was added hydrogen bromide (Aldrich, 30 wt % solution in acetic acid, 1.0 ml). The reaction mixture was stirred for 3 minutes and diethyl ether (20 ml) was added immediately to precipitate the product. The white solid was allowed to settle to the bottom of the flask and the supernatant hydrogen bromide solution was decanted off with a Pasteur pipette. This process was repeated ten times with ether and the remaining traces of ether removed by evaporation under reduced pressure and drying in vacuo overnight. The product was a white solid (50 mg, 57%). $^1$H NMR (MeOH-d$_4$) δ2.00 (pentet, 2H, J=6.3 Hz), 209–2.33 (m, 2H), 2.52 (t, 2H, J=7.3 Hz), 3.95 (s, 2H, 4.15 (t, 2H, J=5.1 Hz), 4.22 (t, 2H, J=6.2 Hz), 4.63 (m, 1H, 6.97 (d, 1H, J=8.6 Hz), 8.21 (dd, 1H, J=2.1, 9.2 Hz), 8.47 (d, 1H, J=2.1 Hz); mass spectrum (FAB); m/e (relative intensity); 463 (100, M+1), 461 (100, M+1), 379 (10), 339 (10), 269 (15).

Radiolabelling Procedure

Compounds according to the invention were linked to the sulphhydryl groups of the F(ab)' fragment of monoclonal antibody C46.3 using standard methods (see Chemical Modification of Proteins, Means and Feeney, Holden-Day Inc 1971). The absence of free-SH groups after modification was confirmed by the assay of Grassetti and Murray (Arch. Biochem. Biophys. 119, 41–49, (1967)). The number of free hydrazines per F(ab)' fragment was determined by a hydrazone formation assay described by Abrams et al, (J. Nucl. Med. 31, 2022 (1990)).

The modified protein was then radiolabelled following a procedure similar to that described by Abrams et al, (J. Nucl. Med. 31, 2022 (1990)), and using for comparison a direct linking of $^{99m}$Tc to the fragment using the Bremmer method and using the two hydrazino linker molecules 15 and 16.

Biodistribution Studies in Mice

Tumours were grown in 3–4 month old, athymic, nude mice by subcutaneous injection in the rear flank of 10$^6$ LS174T colon carcinoma cells.

The $^{99m}$Tc-labelled fragment conjugates were injected into mice via the retro-orbital sinus. Mice received 5–50 µg of protein and 150–800 µCi of $^{99m}$Tc in a volume of about 300 ul of phosphate-buffered saline. The amount injected per mouse was quantified both by the loss of weight and radioactivity of each syringe, and by the radioactivity taken up by the mouse.

Dissection was done at 4 and at 22 hours. Organs were weighed on an analytical balance and their radioactivity determined on a gamma counter. Organ biodistribution was determined from these measurements using standard methods, with the blood volume of the mouse assumed to be 8%. Additional aliquots (15 ul) of blood were taken at 0.5 and 2 hours for pharmacokinetic studies. All gamma counter values were corrected for radioactive decay by counting retained aliquots of the injected dose at the same time as the organs. Final data are expressed as the mean of five (5) mice per group, (+/–) standard deviation, in the Table below.

From a review of the data presented in Tables 1 and 2, it is clear that the linkers containing a cleavable ester function (compounds 8, 9, 10 and 17) gave improved tumour targeting compared to both direct labelling and to labelling via non-cleavable linkers (compounds 15 and 16). The tumour/blood ratios were significantly higher, due to a combination of retention in the tumour and fast clearance from the blood, as can be seen from the % Injected Dose/gram tissue (Table 2). The disulphide-based linkers (compounds 5 and 7) gave conjugates with rapid blood clearance.

TABLE 1

Organ/Blood Ratios at Dissection Time for Tumour-Bearing Mice
Given C46.3 FAB' $^{99m}$Tc-Labelled Via Linkers vs Direct Means

| | Linker 5 - Fab' MSR = 3.1 | | Linker 7 - Fab' MSR = 0.75 | | Linker 8 - Fab' MSR = 1.5 | | Linker 9 - Fab' MSR = 2.7 | |
|---|---|---|---|---|---|---|---|---|
| Organ | 4 hours | 22 hours | 4 hours | 22 hours | 4 hours | 22 hours | 4 hours | 22 hours |
| Blood | (1.00) | (1.00) | (1.00) | (1.00) | (1.00) | (1.00) | (1.00) | (1.00) |
| Lung | 0.59 ± 0.09 | 1.37 ± 0.40 | 0.50 ± 0.08 | 0.90 ± 0.21 | 1.01 ± 0.27 | 1.60 ± 0.49 | 0.70 ± 0.04 | 1.11 ± 0.10 |
| Spleen | 0.31 ± 0.04 | 1.28 ± 0.44 | 0.34 ± 0.04 | 0.92 ± 0.20 | 0.42 ± 0.15 | 1.61 ± 0.19 | 0.31 ± 0.05 | 1.16 ± 0.14 |
| Liver | 0.63 ± 0.06 | 2.50 ± 0.78 | 0.60 ± 0.08 | 1.28 ± 0.31 | 0.69 ± 0.21 | 2.42 ± 0.57 | 0.59 ± 0.05 | 1.86 ± 0.34 |
| Kidney | 54.6 ± 6.3 | 282 ± 58 | 13.5 ± 2.3 | 61.4 ± 14.5 | 116 ± 23 | 316 ± 63 | 55.9 ± 6.7 | 121 ± 13 |
| Tumour | 1.58 ± 0.38 | 4.41 ± 1.34 | 1.14 ± 0.52 | 2.27 ± 0.72 | 3.01 ± 0.46 | 12.8 ± 1.4 | 2.03 ± 0.69 | 10.9 ± 2.2 |
| Muscle | 0.33 ± 0.18 | 0.80 ± 0.43 | 0.20 ± 0.11 | 0.36 ± 0.08 | 0.20 ± 0.05 | 0.24 ± 0.05 | 0.14 ± 0.02 | 0.18 ± 0.02 |

| | Linker 10 - Fab' MSR = 4.5 | | Linker 12 - Fab' MSR = 0.87 | | Linker 17 - Fab' MSR = 3.0 | |
|---|---|---|---|---|---|---|
| Organ | 4 hours | 22 hours | 4 hours | 22 hours | 4 hours | 22 hours |
| Blood | (1.00) | (1.00) | (1.00) | (1.00) | (1.00) | (1.00) |
| Lung | 0.75 ± 0.33 | 1.47 ± 0.11 | 0.59 ± 0.07 | 0.90 ± 0.25 | 0.77 ± 1.13 | 1.82 ± 0.45 |
| Spleen | 0.37 ± 0.16 | 1.88 ± 0.44 | 0.38 ± 0.08 | 1.09 ± 0.36 | 0.55 ± 0.07 | 3.14 ± 0.89 |
| Liver | 0.77 ± 0.21 | 4.20 ± 1.01 | 0.74 ± 0.18 | 1.91 ± 0.56 | 0.76 ± 0.04 | 5.03 ± 2.51 |
| Kidney | 54.6 ± 4.9 | 254 ± 30 | 23.5 ± 5.3 | 128 ± 33 | 107 ± 7 | 598 ± 200 |
| Tumour | 1.98 ± 0.43 | 15.0 ± 6.1 | 1.55 ± 0.86 | 3.97 ± 2.02 | 2.12 ± 0.81 | 12.8 ± 2.3 |
| Muscle | 0.16 ± 0.03 | 0.35 ± 0.05 | 0.38 ± 0.18 | 0.68 ± 0.18 | 0.73 ± 0.39 | 2.42 ± 1.15 |

| | *Linker 15 - Fab' MSR = 0.62 | | *Linker 16 - Fab' MSR = 0.95 | | *Direct Labelled Fab' | |
|---|---|---|---|---|---|---|
| Organ | 4 hours | 22 hours | 4 hours | 22 hours | 4 hours | 22 hours |
| Blood | not done | (1.00) | not done | (1.00) | (1.00) | (1.00) |
| Lung | | 0.55 ± 0.21 | | 1.12 ± 0.30 | 0.70 ± 0.11 | 0.85 ± 0.09 |
| Spleen | | 0.42 ± 0.08 | | 1.54 ± 0.38 | 0.37 ± 0.05 | 0.71 ± 0.10 |
| Liver | | 0.65 ± 0.06 | | 2.71 ± 0.56 | 0.73 ± 0.05 | 1.53 ± 0.28 |
| Kidney | | 41.5 ± 15.2 | | 155 ± 46 | 69.2 ± 14.1 | 114 ± 14 |
| Tumour | | 2.00 ± 0.59 | | 5.09 ± 1.06 | 2.39 ± 0.55 | 4.02 ± 1.13 |
| Muscle | | 0.24 ± 0.14 | | 0.95 ± 0.41 | 0.17 ± 0.04 | 0.20 ± 0.20 |

Notes:
1. All data are averages from 5 mice ± standard deviation.
2. MSR = Molar Substitution Ratio, the number of hydrazines incorporated per Fab' fragment.
3. *Data from conjugates of non-cleavable linkers and direct labelling shown for comparison.
4. >95% of $^{99m}$Tc was bound by Fab' as assayed by standard thin-layer chromatography techniques used in nuclear medicine.

TABLE 2

% Injected Dose Per Gram Tissue at Dissection Time for Tumour-Bearing
Mice Given C46.3 Fab'$^{99mm}$Tc-Labelled Via Linkers vs Direct Means

| | Linker 5 - Fab' MSR = 3.1 | | Linker 7 - Fab' MSR = 0.75 | | Linker 8 - Fab' MSR = 1.5 | | Linker 9 - Fab' MSR = 2.7 | |
|---|---|---|---|---|---|---|---|---|
| Organ | 4 hours | 22 hours | 4 hours | 22 hours | 4 hours | 22 hours | 4 hours | 22 hours |
| Blood | 1.29 ± 0.13 | 0.23 ± 0.09 | 3.11 ± 0.73 | 0.85 ± 0.10 | 1.95 ± 0.21 | 0.29 ± 0.02 | 2.18 ± 0.20 | 0.35 ± 0.03 |
| Lung | 0.76 ± 0.11 | 0.30 ± 0.06 | 1.50 ± 0.17 | 0.75 ± 0.12 | 1.93 ± 0.38 | 0.47 ± 0.16 | 1.53 ± 0.08 | 0.39 ± 0.06 |
| Spleen | 0.40 ± 0.02 | 0.28 ± 0.09 | 1.05 ± 0.28 | 0.76 ± 0.07 | 0.80 ± 0.19 | 0.47 ± 0.06 | 0.66 ± 0.12 | 0.40 ± 0.07 |
| Liver | 0.81 ± 0.10 | 0.54 ± 0.07 | 1.83 ± 0.27 | 1.06 ± 0.13 | 1.32 ± 0.24 | 0.70 ± 0.16 | 1.28 ± 0.07 | 0.63 ± 0.08 |
| Kidney | 70.1 ± 6.6 | 62.3 ± 11.3 | 40.6 ± 4.0 | 51.0 ± 6.2 | 223 ± 27 | 92.1 ± 20.0 | 121 ± 12 | 41.8 ± 6.7 |
| Tumour | 1.99 ± 0.71 | 0.96 ± 0.16 | 3.43 ± 1.57 | 2.30 ± 0.48 | 5.87 ± 1.03 | 3.72 ± 0.58 | 4.45 ± 1.71 | 3.74 ± 0.65 |
| Muscle | 0.44 ± 0.29 | 0.18 ± 0.13 | 0.58 ± 0.23 | 0.30 ± 0.03 | 0.39 ± 0.04 | 0.07 ± 0.02 | 0.31 ± 0.06 | 0.06 ± 0.01 |

| | Linker 10 - Fab' MSR = 4.5 | | Linker 12 - Fab' MSR = 0.87 | | Linker 17 - Fab' MSR = 3.0 | |
|---|---|---|---|---|---|---|
| Organ | 4 hours | 22 hours | 4 hours | 22 hours | 4 hours | 22 hours |
| Blood | 2.63 ± 0.26 | 0.35 ± 0.06 | 1.92 ± 0.42 | 0.59 ± 0.11 | 1.55 ± 0.15 | 0.24 ± 0.09 |
| Lung | 2.10 ± 0.89 | 0.51 ± 0.12 | 1.11 ± 0.20 | 0.51 ± 0.07 | 1.18 ± 0.19 | 0.40 ± 0.03 |
| Spleen | 1.03 ± 0.35 | 0.64 ± 0.12 | 0.71 ± 0.11 | 0.62 ± 0.13 | 0.86 ± 0.14 | 0.69 ± 0.10 |
| Liver | 2.14 ± 0.46 | 1.43 ± 0.20 | 1.37 ± 0.15 | 1.09 ± 0.17 | 1.18 ± 0.17 | 10.5 ± 0.36 |
| Kidney | 154 ± 15 | 87.6 ± 11.5 | 43.4 ± 4.6 | 72.9 ± 10.0 | 167 ± 23 | 127 ± 14 |
| Tumour | 5.38 ± 0.83 | 5.18 ± 1.60 | 2.83 ± 1.41 | 2.19 ± 0.62 | 3.29 ± 1.23 | 2.88 ± 0.57 |

TABLE 2-continued

% Injected Dose Per Gram Tissue at Dissection Time for Tumour-Bearing Mice Given C46.3 Fab'[99mTc]-Labelled Via Linkers vs Direct Means

| Muscle | 0.44 ± 0.08 | 0.12 ± 0.01 | 0.74 ± 0.37 | 0.39 ± 0.05 | 1.17 ± 0.69 | 0.56 ± 0.27 |

| | *Linker 15 - Fab' MSR = 0.62 | | *Linker 16 - Fab' MSR = 0.95 | | *Direct Labelled Fab' | |
| --- | --- | --- | --- | --- | --- | --- |
| Organ | 4 hours | 22 hours | 4 hours | 22 hours | 4 hours | 22 hours |
| Blood | not done | 2.69 ± 0.29 | not done | 0.72 ± 0.12 | 1.65 ± 0.10 | 035 ± 0.04 |
| Lung |  | 1.48 ± 0.57 |  | 0.79 ± 0.19 | 1.15 ± 0.18 | 0.30 ± 0.03 |
| Spleen |  | 1.12 ± 0.10 |  | 1.10 ± 0.28 | 0.62 ± 0.08 | 0.25 ± 0.04 |
| Liver |  | 1.72 ± 0.17 |  | 1.91 ± 0.31 | 1.21 ± 0.10 | 0.53 ± 0.10 |
| Kidney |  | 104 ± 20 |  | 117 ± 23 | 114 ± 23 | 40.1 ± 5.8 |
| Tumour |  | 5.25 ± 1.00 |  | 3.62 ± 0.72 | 3.97 ± 1.04 | 1.41 ± 0.41 |
| Muscle |  | 0.62 ± 0.28 |  | 0.72 ± 0.40 | 0.28 ± 0.06 | 0.07 ± 0.01 |

Notes:
1. All data at averages from 5 mice ± standard deviation.
2. MSR = Molar Substitution Ratio, the number of hydrazines incorporated per Fab' fragment.
3. *Data from conjugates of non-cleavable linkers and direct labelling shown for comparison.
4. >95% of $^{99m}$Tc was bound by Fab' as assayed by standard thin-layer chromatography techniques used in nuclear medicine.

We claim:

1. A compound of formula I,

ENNH—[pyridine]—J—T—Q—Z   (I)

in which

E is an alkylidene group or represent $H_2$ in which case the compound is in an acid addition salt form, J is selected from —CO—NH—, CO—O—, —CO—S— and —NH—CO—, T is an alkylene chain, or, if J is —CO—NH—, T is the residue of an amino acid moiety, Q is a hydrophilic moiety or a moiety cleavable by metabolism in normal body organs and blood, and Z is an amine- and/or thiol-reactive moiety, or Q and Z together form a group which has both hydrophilic or cleavable and amine- and/or thiol-reactive functions.

2. A compound according to claim 1 wherein E represents a straight or branched chain lower alkylidene group.

3. A compound according to claim 1 or 2 wherein -Q-Z is α-bromoacetyl, α-bromoacetamidyl or a mixed substituted or unsubstituted pyridyl disulphide.

4. A compound of formula Ia,

ENNH—[pyridine]—CO—NH—CH(COOH)—C(R)$_2$—S—S—[pyridine]—R'   Ia wherein

E is alkenyl or $H_2$,

R is H or $CH_3$, and

R' is H or $NO_2$.

5. The compound of claim 1 which is:

[structure: $H_2N$-NH-pyridine-CO-NH-CH(CH$_2$COOH)-CO-OSu]

or its acid addition salt wherein Su represents succinimidyl.

6. The compound of claim 1 which is:

[structure: $H_2N$-NH-pyridine-CO-NH-CH(CH$_2$COOH)-CO-NH-CH(CH$_2$CH$_2$COOH)-CO-OSu]

or its acid addition salt wherein Su represents succinimidyl.

7. The compound of claim 1 which is:

[structure: CH$_3$-CH=N-NH-pyridine-CO-NH-(CH$_2$)$_3$-O-CO-CH$_2$CH$_2$-CO-OSu]

or its acid addition salt wherein Su represents succinimidyl.

8. The compound of claim 1 which is:

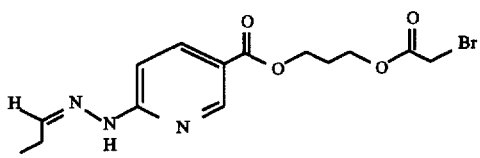

or its acid addition salt.

9. The compound of claim 1 which is:

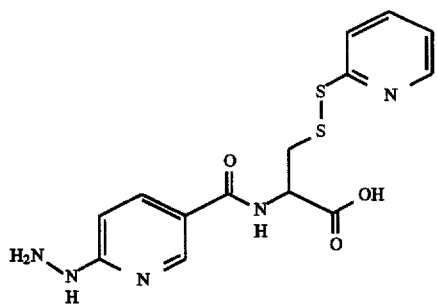

or its acid addition salt.

10. The compound of claim 1 which is:

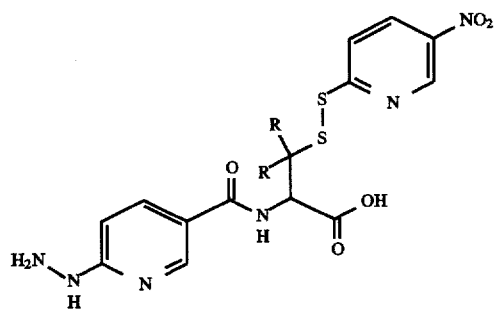

or its acid addition salt and wherein R is H or $CH_3$.

11. The compound of claim 1 which is:

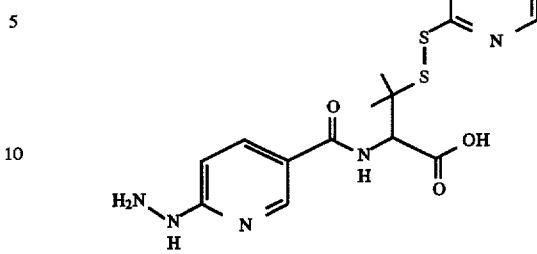

or its acid addition salt.

12. The compound of claim 1 which is:

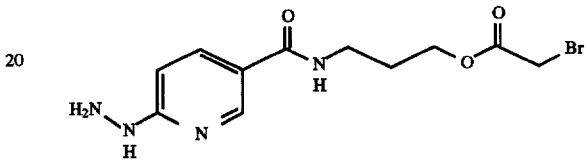

or its acid addition salt.

13. The compound of claim 1 which is:

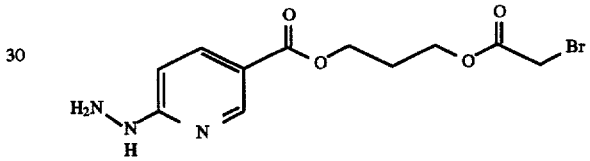

or its acid addition salt.

14. The compound of claim 1 which is:

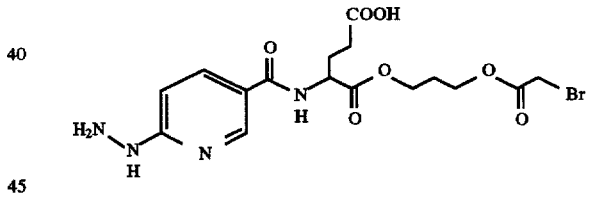

or its acid addition salt.

15. The compound of claim 1 which is:

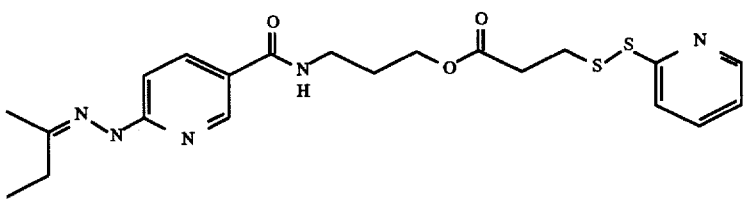

16. The compound of claim 1 which is:

[structure: H2N-NH-pyridine-C(O)NH-CH2CH2-S-C(O)-CH2Br]

or its acid addition salt.

17. The compound of claim 1 which is:

[structure: CH3CH=N-NH-pyridine-C(O)NH-CH2CH2-S-S-CH2CH2-C(O)-OSu]

or its acid addition salt wherein Su represents succinimidyl.

18. The compound of claim 1 which is:

[structure with COOH side chain: H2N-NH-pyridine-C(O)NH-CH(CH2CH2COOH)-C(O)NH-CH2CH2-S-S-CH2CH2-C(O)-OSu]

or its acid addition salt wherein Su represents succinimidyl.

19. The compound of claim 1 which is:

[structure: H2NNH-pyridine-NHCO-(CH2)2-S-S-pyridine]

or its acid addition salt.

20. The compound of claim 1 which is:

[structure: H2N-NH-pyridine-COO-(CH2)3-NHCO-CH2Br]

or its acid addition salt.

21. The compound of claim 1 which is:

[structure: H2NNH-pyridine-CONH-CH(COOH)-CH2CH2-C(O)-O-(CH2)3-O-C(O)-CH2Br]

or its acid addition salt.

22. A conjugate comprising the reaction product of a macromolecule with a compound according to claim 1.

23. A conjugate according to claim 22, wherein the macromolecule comprises an immunoglobulin or a fragment thereof.

24. A labelled macromolecule comprising a metal atom bound to a conjugate according to claim 22.

25. A labelled macromolecule according to claim 24, wherein the metal is selected from radioisotopes of Tc and Re.

26. A compound of formula II $$\text{ENNH}-\text{pyridine}-\text{CONH}-(\text{CH}_2)_2-\text{S}-\text{S}-\text{pyridine} \quad (\text{II})$$

in which E is alkenyl or $H_2$.

27. A compound of formula

[structure with ENNH-pyridine-C(O)-X-C(R1)(Z)-C(R2)(R3)-(n)-Y]

in which

E is an alkylidene group or represents $H_2$ in which case the compound is in acid addition salt form, X is selected from O and NH, one or both of Y and Z comprise an amine or thiol reactive moiety and a hydrophilic moiety or a moiety cleavable by metabolism in normal organs or blood, n indicates an alkylene chain, and $R^1$–$R^3$ are selected from H and methyl.

* * * * *